(12) United States Patent
Becking et al.

(10) Patent No.: US 9,095,342 B2
(45) Date of Patent: Aug. 4, 2015

(54) BRAID BALL EMBOLIC DEVICE FEATURES

(75) Inventors: Frank P. Becking, Palo Alto, CA (US);
Nicholas C. deBeer, Montar, CA (US);
Siddharth Loganathan, Mountain View, CA (US)

(73) Assignee: Covidien LP, Mansfield, MA (US)

( * ) Notice: Subject to any disclaimer, the term of this patent is extended or adjusted under 35 U.S.C. 154(b) by 137 days.

(21) Appl. No.: 12/942,209

(22) Filed: Nov. 9, 2010

(65) Prior Publication Data

US 2011/0319926 A1    Dec. 29, 2011

Related U.S. Application Data

(60) Provisional application No. 61/259,585, filed on Nov. 9, 2009.

(51) Int. Cl.
*A61M 29/00* (2006.01)
*A61B 17/12* (2006.01)
*A61B 19/00* (2006.01)
*A61B 17/00* (2006.01)

(52) U.S. Cl.
CPC ..... *A61B 17/12022* (2013.01); *A61B 17/12109* (2013.01); *A61B 17/12113* (2013.01); *A61B 17/12172* (2013.01); *A61B 17/0057* (2013.01); *A61B 19/54* (2013.01)

(58) Field of Classification Search
CPC .................. A61B 17/12022; A61B 17/12113; A61B 17/12109; A61B 2017/12054; A61B 19/54; A61M 2025/1079
USPC ......... 606/200, 113, 114, 127, 151, 153, 157, 606/159, 191, 194; 604/48, 104, 103.1, 529
See application file for complete search history.

(56) References Cited

U.S. PATENT DOCUMENTS

| | | | |
|---|---|---|---|
| 4,425,908 A | 1/1984 | Simon | |
| 4,619,246 A | 10/1986 | Molgaard-Nielsen et al. | |
| 4,655,771 A | 4/1987 | Wallsten | |
| 4,768,507 A | 9/1988 | Fischell et al. | |
| 4,921,484 A * | 5/1990 | Hillstead | 604/104 |
| 4,998,539 A | 3/1991 | Delsanti | |
| 5,026,377 A | 6/1991 | Burton et al. | |
| 5,061,275 A | 10/1991 | Wallsten et al. | |
| 5,064,435 A | 11/1991 | Porter | |

(Continued)

FOREIGN PATENT DOCUMENTS

| | | |
|---|---|---|
| CN | 101472537 A | 7/2009 |
| DE | 102008028308 | 4/2009 |

(Continued)

OTHER PUBLICATIONS

U.S. Appl. No. 60/948,683, filed Jul. 9, 2007.

(Continued)

*Primary Examiner* — Katherine Dowe
*Assistant Examiner* — Sidharth Kapoor
(74) *Attorney, Agent, or Firm* — Elizabeth A. O'Brien, Esq.

(57) ABSTRACT

Embolic implants and methods of manufacture are disclosed. The implants may be used for occluding blood flow at endovascular sites. One use is in intracranial aneurysm emolization/occlusion and another in parent vessel occlusion (PVO) or sacrifice. Various features provide for improved use (e.g., regarding delivery, recapture, visualization and/or occlusion) and manufacturability.

22 Claims, 10 Drawing Sheets

(56) References Cited

U.S. PATENT DOCUMENTS

| | | | |
|---|---|---|---|
| 5,104,404 A | 4/1992 | Wolff | |
| 5,122,136 A | 6/1992 | Guglielmi et al. | |
| 5,222,971 A | 6/1993 | Willard et al. | |
| 5,250,071 A | 10/1993 | Palermo | |
| 5,334,210 A * | 8/1994 | Gianturco | 606/151 |
| 5,378,239 A | 1/1995 | Termin et al. | |
| 5,405,379 A | 4/1995 | Lane | |
| 5,425,984 A | 6/1995 | Kennedy et al. | |
| 5,484,444 A | 1/1996 | Braunschweiler et al. | |
| 5,499,981 A | 3/1996 | Kordis | |
| 5,527,338 A | 6/1996 | Purdy | |
| 5,545,208 A | 8/1996 | Wolff et al. | |
| 5,549,635 A | 8/1996 | Solar | |
| 5,624,461 A | 4/1997 | Mariant | |
| 5,634,942 A | 6/1997 | Chevillon et al. | |
| 5,645,558 A | 7/1997 | Horton | |
| 5,690,671 A | 11/1997 | McGurk et al. | |
| 5,725,552 A | 3/1998 | Kotula et al. | |
| 5,728,906 A | 3/1998 | Eguchi et al. | |
| 5,733,294 A | 3/1998 | Forber et al. | |
| 5,741,333 A | 4/1998 | Frid | |
| 5,749,891 A | 5/1998 | Ken et al. | |
| 5,749,919 A | 5/1998 | Blanc | |
| 5,749,920 A | 5/1998 | Quiachon et al. | |
| 5,766,151 A | 6/1998 | Valley et al. | |
| 5,814,062 A | 9/1998 | Sepetka et al. | |
| 5,830,230 A | 11/1998 | Berryman et al. | |
| 5,846,261 A | 12/1998 | Kotula et al. | |
| 5,879,366 A | 3/1999 | Shaw et al. | |
| 5,911,731 A | 6/1999 | Pham et al. | |
| 5,916,235 A | 6/1999 | Guglielmi | |
| 5,925,060 A | 7/1999 | Forber | |
| 5,928,228 A | 7/1999 | Kordis et al. | |
| 5,928,260 A | 7/1999 | Chin et al. | |
| 5,935,148 A | 8/1999 | Villar et al. | |
| 5,935,362 A | 8/1999 | Petrick | |
| 5,941,249 A | 8/1999 | Maynard | |
| 5,944,738 A | 8/1999 | Amplatz et al. | |
| 5,951,599 A | 9/1999 | McCrory | |
| 5,957,948 A | 9/1999 | Mariant | |
| 5,980,554 A | 11/1999 | Lenker et al. | |
| 6,010,517 A | 1/2000 | Baccaro | |
| 6,024,756 A | 2/2000 | Huebsch et al. | |
| 6,033,423 A | 3/2000 | Ken et al. | |
| 6,036,720 A | 3/2000 | Abrams et al. | |
| 6,063,070 A | 5/2000 | Eder | |
| 6,063,104 A | 5/2000 | Villar et al. | |
| 6,086,577 A | 7/2000 | Ken et al. | |
| 6,093,199 A | 7/2000 | Brown et al. | |
| 6,096,034 A | 8/2000 | Kupiecki et al. | |
| 6,096,073 A | 8/2000 | Webster et al. | |
| 6,099,526 A | 8/2000 | Whayne et al. | |
| 6,123,715 A | 9/2000 | Amplatz | |
| 6,139,564 A | 10/2000 | Teoh | |
| 6,152,144 A | 11/2000 | Lesh et al. | |
| 6,168,592 B1 | 1/2001 | Kupiecki et al. | |
| 6,168,615 B1 | 1/2001 | Ken et al. | |
| 6,168,618 B1 | 1/2001 | Frantzen | |
| 6,168,622 B1 | 1/2001 | Mazzocchi | |
| 6,183,495 B1 | 2/2001 | Lenker et al. | |
| 6,190,402 B1 | 2/2001 | Horton et al. | |
| 6,193,708 B1 | 2/2001 | Ken et al. | |
| 6,221,086 B1 | 4/2001 | Forber | |
| 6,261,305 B1 | 7/2001 | Marotta et al. | |
| 6,306,141 B1 | 10/2001 | Jervis | |
| 6,309,367 B1 | 10/2001 | Boock | |
| 6,322,576 B1 | 11/2001 | Wallace et al. | |
| 6,325,820 B1 | 12/2001 | Khosravi et al. | |
| 6,331,184 B1 | 12/2001 | Abrams | |
| 6,332,576 B1 | 12/2001 | Colley et al. | |
| 6,342,068 B1 | 1/2002 | Thompson | |
| 6,344,041 B1 | 2/2002 | Kupiecki et al. | |
| 6,344,048 B1 | 2/2002 | Chin et al. | |
| 6,346,117 B1 | 2/2002 | Greenhalgh | |
| 6,350,270 B1 | 2/2002 | Roue | |
| 6,361,558 B1 | 3/2002 | Hieshima et al. | |
| 6,368,339 B1 | 4/2002 | Amplatz | |
| 6,375,668 B1 | 4/2002 | Gifford et al. | |
| 6,383,174 B1 | 5/2002 | Eder | |
| 6,391,037 B1 | 5/2002 | Greenhalgh | |
| 6,409,750 B1 | 6/2002 | Hyodoh et al. | |
| 6,428,558 B1 | 8/2002 | Jones et al. | |
| 6,443,972 B1 | 9/2002 | Bosma et al. | |
| 6,447,531 B1 | 9/2002 | Amplatz | |
| 6,454,780 B1 | 9/2002 | Wallace | |
| 6,506,204 B2 | 1/2003 | Mazzocchi | |
| 6,511,468 B1 * | 1/2003 | Cragg et al. | 604/508 |
| 6,530,934 B1 | 3/2003 | Jacobsen et al. | |
| 6,547,804 B2 | 4/2003 | Porter et al. | |
| 6,551,303 B1 | 4/2003 | Van Tassel et al. | |
| 6,569,179 B2 | 5/2003 | Teoh et al. | |
| 6,579,303 B2 | 6/2003 | Amplatz | |
| 6,585,748 B1 | 7/2003 | Jeffree | |
| 6,585,756 B1 | 7/2003 | Strecker | |
| 6,589,256 B2 | 7/2003 | Forber | |
| 6,589,265 B1 | 7/2003 | Palmer et al. | |
| 6,592,605 B2 | 7/2003 | Lenker et al. | |
| 6,599,308 B2 | 7/2003 | Amplatz | |
| 6,605,102 B1 | 8/2003 | Mazzocchi et al. | |
| 6,605,111 B2 | 8/2003 | Bose et al. | |
| 6,607,551 B1 | 8/2003 | Sullivan et al. | |
| 6,613,074 B1 | 9/2003 | Mitelberg et al. | |
| 6,626,939 B1 | 9/2003 | Burnside et al. | |
| 6,632,241 B1 | 10/2003 | Hancock et al. | |
| 6,635,068 B1 | 10/2003 | Dubrul et al. | |
| 6,635,069 B1 | 10/2003 | Teoh et al. | |
| 6,652,555 B1 | 11/2003 | VanTassel et al. | |
| 6,652,556 B1 * | 11/2003 | VanTassel et al. | 606/200 |
| 6,666,882 B1 | 12/2003 | Bose et al. | |
| 6,666,883 B1 | 12/2003 | Seguin et al. | |
| 6,669,717 B2 | 12/2003 | Marotta et al. | |
| 6,669,721 B1 | 12/2003 | Bose et al. | |
| 6,676,696 B1 | 1/2004 | Marotta et al. | |
| 6,682,505 B2 | 1/2004 | Bates et al. | |
| 6,682,546 B2 | 1/2004 | Amplatz | |
| 6,689,150 B1 | 2/2004 | VanTassel et al. | |
| 6,689,486 B2 | 2/2004 | Ho et al. | |
| 6,695,876 B1 | 2/2004 | Marotta et al. | |
| 6,698,877 B2 | 3/2004 | Urlaub et al. | |
| 6,699,274 B2 | 3/2004 | Stinson | |
| 6,712,835 B2 | 3/2004 | Mazzocchi et al. | |
| 6,723,112 B2 | 4/2004 | Ho et al. | |
| 6,723,116 B2 | 4/2004 | Taheri | |
| 6,730,108 B2 | 5/2004 | Van Tassel et al. | |
| 6,746,468 B1 | 6/2004 | Sepetka et al. | |
| 6,746,890 B2 | 6/2004 | Gupta et al. | |
| 6,780,196 B2 | 8/2004 | Chin et al. | |
| 6,792,979 B2 | 9/2004 | Konya et al. | |
| 6,797,083 B2 | 9/2004 | Peterson | |
| 6,802,851 B2 | 10/2004 | Jones et al. | |
| RE38,653 E | 11/2004 | Igaki et al. | |
| 6,811,560 B2 | 11/2004 | Jones et al. | |
| 6,855,153 B2 | 2/2005 | Saadat | |
| 6,855,154 B2 | 2/2005 | Abdel-Gawwad | |
| RE38,711 E | 3/2005 | Igaki et al. | |
| 6,860,893 B2 | 3/2005 | Wallace et al. | |
| 6,936,055 B1 | 8/2005 | Ken et al. | |
| 6,949,103 B2 | 9/2005 | Mazzocchi et al. | |
| 6,949,113 B2 | 9/2005 | Van Tassel et al. | |
| 6,953,472 B2 | 10/2005 | Palmer et al. | |
| 6,979,341 B2 | 12/2005 | Scribner et al. | |
| 6,989,019 B2 | 1/2006 | Mazzocchi et al. | |
| 6,994,092 B2 | 2/2006 | van der Burg et al. | |
| 6,994,717 B2 | 2/2006 | Kónya et al. | |
| 7,011,671 B2 | 3/2006 | Welch | |
| 7,018,401 B1 | 3/2006 | Hyodoh et al. | |
| 7,029,487 B2 | 4/2006 | Greene, Jr. et al. | |
| 7,033,375 B2 | 4/2006 | Mazzocchi et al. | |
| 7,048,752 B2 | 5/2006 | Mazzocchi et al. | |
| 7,063,679 B2 | 6/2006 | Maguire et al. | |
| 7,070,607 B2 | 7/2006 | Murayama et al. | |
| 7,070,609 B2 | 7/2006 | West | |
| 7,083,632 B2 | 8/2006 | Avellanet et al. | |
| 7,128,073 B1 | 10/2006 | van der Burg et al. | |

(56) References Cited

U.S. PATENT DOCUMENTS

| | | |
|---|---|---|
| 7,128,736 B1 | 10/2006 | Abrams et al. |
| 7,169,177 B2 | 1/2007 | Obara |
| 7,195,636 B2 | 3/2007 | Avellanet et al. |
| 7,211,109 B2 | 5/2007 | Thompson |
| 7,229,461 B2 | 6/2007 | Chin et al. |
| 7,232,461 B2 | 6/2007 | Ramer |
| 7,261,720 B2 | 8/2007 | Stevens et al. |
| 7,303,571 B2 | 12/2007 | Makower et al. |
| 7,306,622 B2 | 12/2007 | Jones et al. |
| 7,331,980 B2 | 2/2008 | Dubrul et al. |
| 7,367,985 B2 | 5/2008 | Mazzocchi et al. |
| 7,367,986 B2 | 5/2008 | Mazzocchi et al. |
| 7,371,250 B2 | 5/2008 | Mazzocchi et al. |
| 7,404,820 B2 | 7/2008 | Mazzocchi et al. |
| 7,410,482 B2 | 8/2008 | Murphy et al. |
| 7,410,492 B2 | 8/2008 | Mazzocchi et al. |
| 7,413,622 B2 | 8/2008 | Peterson |
| 7,419,503 B2 | 9/2008 | Pulnev et al. |
| 7,442,200 B2 | 10/2008 | Mazzocchi et al. |
| 7,485,088 B2 | 2/2009 | Murphy et al. |
| 7,556,635 B2 | 7/2009 | Mazzocchi et al. |
| 7,566,338 B2 | 7/2009 | Mazzocchi et al. |
| 7,569,066 B2 | 8/2009 | Gerberding et al. |
| 7,572,273 B2 | 8/2009 | Mazzocchi et al. |
| 7,572,288 B2 | 8/2009 | Cox |
| 7,597,704 B2 | 10/2009 | Frazier et al. |
| 7,608,088 B2 | 10/2009 | Jones et al. |
| 7,621,928 B2 | 11/2009 | Thramann et al. |
| 7,670,355 B2 | 3/2010 | Mazzocchi et al. |
| 7,670,356 B2 | 3/2010 | Mazzocchi et al. |
| 7,678,130 B2 | 3/2010 | Mazzocchi et al. |
| 7,682,390 B2 | 3/2010 | Seguin |
| 7,691,124 B2 | 4/2010 | Balgobin |
| 7,695,488 B2 | 4/2010 | Berenstein et al. |
| 7,699,056 B2 | 4/2010 | Tran et al. |
| 7,727,189 B2 | 6/2010 | VanTassel et al. |
| 7,744,583 B2 | 6/2010 | Seifert et al. |
| 7,744,652 B2 | 6/2010 | Morsi |
| 7,763,011 B2 | 7/2010 | Ortiz et al. |
| 7,828,815 B2 | 11/2010 | Mazzocchi et al. |
| 7,828,816 B2 | 11/2010 | Mazzocchi et al. |
| 7,906,066 B2 | 3/2011 | Wilson et al. |
| 7,922,732 B2 | 4/2011 | Mazzocchi et al. |
| 7,955,343 B2 | 6/2011 | Makower et al. |
| 7,972,359 B2 | 7/2011 | Kreidler |
| 7,993,364 B2 | 8/2011 | Morsi |
| RE42,758 E | 9/2011 | Ken et al. |
| 8,062,379 B2 | 11/2011 | Morsi |
| 8,075,585 B2 | 12/2011 | Lee et al. |
| 8,142,456 B2 | 3/2012 | Rosqueta et al. |
| 8,202,280 B2 | 6/2012 | Richter |
| 8,221,445 B2 | 7/2012 | van Tassel et al. |
| 8,261,648 B1 | 9/2012 | Marchand et al. |
| 8,298,257 B2 | 10/2012 | Sepetka et al. |
| 8,430,012 B1 | 4/2013 | Marchand et al. |
| 2001/0000797 A1 | 5/2001 | Mazzocchi |
| 2001/0012949 A1 | 8/2001 | Forber |
| 2001/0051822 A1 | 12/2001 | Stack et al. |
| 2002/0013599 A1 | 1/2002 | Limon et al. |
| 2002/0013618 A1 | 1/2002 | Marotta et al. |
| 2002/0042628 A1 | 4/2002 | Chin et al. |
| 2002/0062091 A1 | 5/2002 | Jacobsen et al. |
| 2002/0165572 A1* | 11/2002 | Saadat ............... 606/194 |
| 2002/0169473 A1 | 11/2002 | Sepetka et al. |
| 2003/0004538 A1 | 1/2003 | Secrest et al. |
| 2003/0028209 A1 | 2/2003 | Teoh et al. |
| 2003/0057156 A1 | 3/2003 | Peterson et al. |
| 2003/0171739 A1 | 9/2003 | Murphy et al. |
| 2003/0176884 A1* | 9/2003 | Berrada et al. ............... 606/200 |
| 2003/0195553 A1 | 10/2003 | Wallace et al. |
| 2003/0199913 A1 | 10/2003 | Dubrul et al. |
| 2003/0199919 A1 | 10/2003 | Palmer et al. |
| 2004/0015224 A1 | 1/2004 | Armstrong et al. |
| 2004/0034386 A1 | 2/2004 | Fulton et al. |
| 2004/0044391 A1 | 3/2004 | Porter |
| 2004/0098027 A1 | 5/2004 | Teoh et al. |
| 2004/0098030 A1 | 5/2004 | Makower et al. |
| 2004/0106945 A1 | 6/2004 | Thramann et al. |
| 2004/0106977 A1 | 6/2004 | Sullivan et al. |
| 2004/0111112 A1 | 6/2004 | Hoffmann |
| 2004/0122467 A1 | 6/2004 | VanTassel et al. |
| 2004/0122468 A1 | 6/2004 | Yodfat et al. |
| 2004/0143286 A1 | 7/2004 | Johnson et al. |
| 2004/0162606 A1 | 8/2004 | Thompson |
| 2004/0172056 A1 | 9/2004 | Guterman et al. |
| 2004/0181253 A1 | 9/2004 | Sepetka et al. |
| 2004/0186562 A1 | 9/2004 | Cox |
| 2004/0193206 A1 | 9/2004 | Gerberding et al. |
| 2004/0215332 A1 | 10/2004 | Frid |
| 2004/0249408 A1 | 12/2004 | Murphy et al. |
| 2004/0267346 A1 | 12/2004 | Shelso |
| 2005/0010281 A1 | 1/2005 | Yodfat et al. |
| 2005/0021077 A1 | 1/2005 | Chin et al. |
| 2005/0033408 A1 | 2/2005 | Jones et al. |
| 2005/0033409 A1 | 2/2005 | Burke et al. |
| 2005/0060017 A1 | 3/2005 | Fischell et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131443 A1 | 6/2005 | Abdel-Gawwad |
| 2005/0228434 A1 | 10/2005 | Amplatz et al. |
| 2005/0267568 A1 | 12/2005 | Berez et al. |
| 2005/0273135 A1 | 12/2005 | Chanduszko et al. |
| 2006/0052816 A1 | 3/2006 | Bates |
| 2006/0064151 A1 | 3/2006 | Guterman et al. |
| 2006/0106421 A1 | 5/2006 | Teoh |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0167494 A1 | 7/2006 | Suddaby |
| 2006/0190070 A1 | 8/2006 | Dieck et al. |
| 2006/0190076 A1 | 8/2006 | Taheri |
| 2006/0206199 A1 | 9/2006 | Churchwell et al. |
| 2006/0206200 A1 | 9/2006 | Garcia et al. |
| 2006/0235464 A1 | 10/2006 | Avellanet et al. |
| 2006/0235501 A1 | 10/2006 | Igaki |
| 2006/0241690 A1 | 10/2006 | Amplatz et al. |
| 2006/0247680 A1 | 11/2006 | Amplatz et al. |
| 2006/0264905 A1 | 11/2006 | Eskridge et al. |
| 2006/0264907 A1 | 11/2006 | Eskridge et al. |
| 2006/0271149 A1 | 11/2006 | Berez et al. |
| 2006/0271153 A1 | 11/2006 | Garcia et al. |
| 2006/0276827 A1 | 12/2006 | Mitelberg et al. |
| 2006/0292206 A1 | 12/2006 | Kim et al. |
| 2006/0293744 A1 | 12/2006 | Peckham et al. |
| 2007/0005125 A1 | 1/2007 | Berenstein et al. |
| 2007/0016243 A1 | 1/2007 | Ramaiah et al. |
| 2007/0021816 A1 | 1/2007 | Rudin |
| 2007/0088387 A1 | 4/2007 | Eskridge et al. |
| 2007/0093889 A1 | 4/2007 | Wu et al. |
| 2007/0106311 A1 | 5/2007 | Wallace et al. |
| 2007/0135826 A1* | 6/2007 | Zaver et al. ............... 606/157 |
| 2007/0150045 A1 | 6/2007 | Ferrera |
| 2007/0162104 A1 | 7/2007 | Frid |
| 2007/0173928 A1 | 7/2007 | Morsi |
| 2007/0191884 A1 | 8/2007 | Eskridge et al. |
| 2007/0191924 A1 | 8/2007 | Rudakov |
| 2007/0198075 A1 | 8/2007 | Levy |
| 2007/0203567 A1 | 8/2007 | Levy |
| 2007/0219619 A1 | 9/2007 | Dieck et al. |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0233244 A1 | 10/2007 | Lopez et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2008/0009934 A1 | 1/2008 | Schneider et al. |
| 2008/0021535 A1 | 1/2008 | Leopold et al. |
| 2008/0039933 A1 | 2/2008 | Yodfat et al. |
| 2008/0045996 A1 | 2/2008 | Makower et al. |
| 2008/0045997 A1 | 2/2008 | Balgobin et al. |
| 2008/0058856 A1 | 3/2008 | Ramaiah et al. |

(56) References Cited

U.S. PATENT DOCUMENTS

| | | |
|---|---|---|
| 2008/0065145 A1 | 3/2008 | Carpenter |
| 2008/0097495 A1 | 4/2008 | Feller, III et al. |
| 2008/0109063 A1 | 5/2008 | Hancock et al. |
| 2008/0114391 A1 | 5/2008 | Dieck et al. |
| 2008/0114436 A1 | 5/2008 | Dieck et al. |
| 2008/0114439 A1 | 5/2008 | Ramaiah et al. |
| 2008/0119886 A1 | 5/2008 | Greenhalgh et al. |
| 2008/0125806 A1 | 5/2008 | Mazzocchi et al. |
| 2008/0140177 A1 | 6/2008 | Hines |
| 2008/0154286 A1 | 6/2008 | Abbott et al. |
| 2008/0195139 A1 | 8/2008 | Donald et al. |
| 2008/0219533 A1 | 9/2008 | Grigorescu |
| 2008/0221600 A1 | 9/2008 | Dieck et al. |
| 2008/0249562 A1 | 10/2008 | Cahill |
| 2008/0281350 A1* | 11/2008 | Sepetka et al. ................ 606/200 |
| 2008/0319533 A1 | 12/2008 | Lehe |
| 2009/0025820 A1 | 1/2009 | Adams |
| 2009/0069806 A1 | 3/2009 | De La Mora Levy et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0118811 A1 | 5/2009 | Moloney |
| 2009/0143851 A1 | 6/2009 | Paul, Jr. |
| 2009/0198315 A1 | 8/2009 | Boudjemline |
| 2009/0210047 A1 | 8/2009 | Amplatz et al. |
| 2009/0216307 A1 | 8/2009 | Kaufmann et al. |
| 2009/0228029 A1 | 9/2009 | Lee |
| 2009/0259202 A1 | 10/2009 | Leeflang et al. |
| 2009/0264914 A1 | 10/2009 | Riina et al. |
| 2009/0275974 A1* | 11/2009 | Marchand et al. ............ 606/194 |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka et al. |
| 2010/0004726 A1 | 1/2010 | Hancock et al. |
| 2010/0004761 A1 | 1/2010 | Flanders et al. |
| 2010/0023105 A1 | 1/2010 | Levy et al. |
| 2010/0030200 A1 | 2/2010 | Strauss et al. |
| 2010/0042133 A1 | 2/2010 | Ramzipoor et al. |
| 2010/0069948 A1 | 3/2010 | Veznedaroglu et al. |
| 2010/0094335 A1 | 4/2010 | Gerberding et al. |
| 2010/0131002 A1 | 5/2010 | Connor et al. |
| 2010/0152767 A1 | 6/2010 | Greenhalgh et al. |
| 2010/0268260 A1 | 10/2010 | Riina et al. |
| 2010/0274276 A1 | 10/2010 | Chow et al. |
| 2010/0312270 A1 | 12/2010 | McGuckin, Jr. et al. |
| 2010/0331948 A1 | 12/2010 | Turovskiy et al. |
| 2011/0022149 A1 | 1/2011 | Cox et al. |
| 2011/0144669 A1 | 6/2011 | Becking et al. |
| 2011/0152993 A1 | 6/2011 | Marchand et al. |
| 2011/0184452 A1 | 7/2011 | Huynh et al. |
| 2011/0184453 A1 | 7/2011 | Levy et al. |
| 2011/0196415 A1 | 8/2011 | Ujiie et al. |
| 2011/0202085 A1 | 8/2011 | Loganathan et al. |
| 2011/0208227 A1 | 8/2011 | Becking |
| 2011/0245862 A1 | 10/2011 | Dieck et al. |
| 2011/0265943 A1 | 11/2011 | Rosqueta et al. |
| 2011/0313447 A1 | 12/2011 | Strauss et al. |
| 2012/0041470 A1 | 2/2012 | Shrivastava et al. |
| 2012/0065720 A1 | 3/2012 | Strauss et al. |
| 2012/0143237 A1 | 6/2012 | Cam et al. |
| 2012/0143317 A1 | 6/2012 | Cam et al. |
| 2012/0165803 A1 | 6/2012 | Bencini et al. |
| 2012/0165919 A1 | 6/2012 | Cox et al. |
| 2012/0197283 A1 | 8/2012 | Marchand et al. |
| 2012/0245674 A1 | 9/2012 | Molaei et al. |
| 2012/0245675 A1 | 9/2012 | Molaei et al. |
| 2012/0283768 A1 | 11/2012 | Cox et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2013/0066360 A1 | 3/2013 | Becking et al. |
| 2013/0085522 A1 | 4/2013 | Becking et al. |
| 2013/0092013 A1 | 4/2013 | Thompson et al. |
| 2013/0123830 A1 | 5/2013 | Becking et al. |
| 2013/0211495 A1 | 8/2013 | Halden et al. |
| 2013/0233160 A1 | 9/2013 | Marchand et al. |
| 2013/0239790 A1 | 9/2013 | Thompson et al. |
| 2013/0245667 A1 | 9/2013 | Marchand et al. |
| 2013/0268053 A1 | 10/2013 | Molaei et al. |
| 2013/0274862 A1 | 10/2013 | Cox et al. |
| 2013/0274863 A1 | 10/2013 | Cox et al. |
| 2013/0274866 A1 | 10/2013 | Cox et al. |
| 2013/0274868 A1 | 10/2013 | Cox et al. |

FOREIGN PATENT DOCUMENTS

| | | |
|---|---|---|
| EP | 775470 | 5/1997 |
| EP | 855170 A2 | 7/1998 |
| EP | 1621148 A1 | 2/2006 |
| EP | 1637176 | 3/2006 |
| EP | 1752112 | 2/2007 |
| EP | 1942972 | 7/2008 |
| EP | 1872742 B1 | 5/2009 |
| EP | 2279023 A2 | 2/2011 |
| EP | 2363075 | 9/2011 |
| EP | 2496299 A2 | 9/2012 |
| EP | 2675402 A2 | 12/2013 |
| FR | 2556210 B1 | 4/1988 |
| FR | 2890306 | 3/2007 |
| JP | 11-506686 | 6/1999 |
| JP | 2003520103 A | 7/2003 |
| JP | 2003-524434 A | 8/2003 |
| JP | 2004-049585 A | 2/2004 |
| JP | 2005-522266 A | 7/2005 |
| JP | 2006-506201 A | 2/2006 |
| JP | 2008-541832 A | 11/2008 |
| JP | 4673987 B2 | 4/2011 |
| WO | WO-88/00813 | 2/1988 |
| WO | WO-96/01591 | 1/1996 |
| WO | WO 97/26939 A1 | 7/1997 |
| WO | WO-99/03404 | 1/1999 |
| WO | WO 99/03404 A1 | 1/1999 |
| WO | WO-99/05977 | 2/1999 |
| WO | WO 99/05977 A1 | 2/1999 |
| WO | WO-99/08607 | 2/1999 |
| WO | WO-99/08743 | 2/1999 |
| WO | WO-99/62432 | 12/1999 |
| WO | WO 99/62432 A1 | 12/1999 |
| WO | WO 01/93782 A1 | 12/2001 |
| WO | WO 02/00139 A1 | 1/2002 |
| WO | WO 02/071977 A2 | 9/2002 |
| WO | WO 2005/117718 A1 | 12/2005 |
| WO | WO 2006/026744 A1 | 3/2006 |
| WO | WO-2006/034166 A2 | 3/2006 |
| WO | WO 2006/052322 A2 | 5/2006 |
| WO | WO 2006/091891 A2 | 8/2006 |
| WO | WO-2006/119422 A2 | 11/2006 |
| WO | WO-2007/047851 A2 | 4/2007 |
| WO | WO-2007/076480 A2 | 7/2007 |
| WO | WO 2007/121405 A2 | 10/2007 |
| WO | WO 2008/022327 A2 | 2/2008 |
| WO | WO 2008/151204 A1 | 12/2008 |
| WO | WO 2008/157507 A2 | 12/2008 |
| WO | WO-2009/076515 | 6/2009 |
| WO | WO 2009/132045 A2 | 10/2009 |
| WO | WO 2009/134337 A1 | 11/2009 |
| WO | WO-2009/135166 A2 | 11/2009 |
| WO | WO-2010/028314 | 3/2010 |
| WO | WO 2010/030991 A1 | 3/2010 |
| WO | WO-2011/057002 A2 | 5/2011 |
| WO | WO 2011/057277 A2 | 5/2011 |
| WO | WO-2011/130081 | 10/2011 |
| WO | WO-2011/153304 | 12/2011 |
| WO | WO-2012/112749 A2 | 8/2012 |

OTHER PUBLICATIONS

U.S. Appl. No. 61/044,822, filed Apr. 14, 2008.
PCT/US, 2009/041313 Partial International Search Report, Sep. 30, 2009.
PCT/US, 2009/041313, International Search Report, Jan. 14, 2010.
CN, Serial No. 200980114155.5 Office Action, Mar. 29, 2012.
EP, Serial No. 11173658.3 EESR, May 8, 2012.

(56) References Cited

OTHER PUBLICATIONS

EP, Serial No. 11173659.1 EESR, May 8, 2012.
EP, Serial No. 11189200.6 EESR, May 8, 2012.
EP, Serial No. 12150960.8 ESR, Jun. 6, 2012.
EP, Serial No. 12150959.0 ESR, Jun. 12, 2012.
EP, Serial No. 11184201.9 EESR, Sep. 5, 2012.
U.S. Appl. No. 12/427,635—Final Office Action, Jan. 31, 2013.
Thorell, et al., "Y-configured Dual Intracranial Stent-assisted Coil Embolization for the Treatment of Wide-necked Basilar Tip Aneurysms", Neurosurgery, May 2005, vol. 56, Issue 5, pp. 1035-1040.
Hill, et al., "Initial Results of the Amplatzer Vascular Plug in the Treatment of Congenital Heart Disease, Business Briefing," US Cardiology 2004.
Ronnen, "Amplatzer Vascular Plug Case Study, Closure of Arteriovenous Fistula Between Deep Femoral Artery and Superficial Femoral Vein," AGA Medical Corporation, May 2007.
U.S. Appl. No. 13/629,678, filed Sep. 28, 2012.
U.S. Appl. No. 13/669,652, filed Nov. 6, 2012.
U.S. Appl. No. 13/826,298, filed Mar. 14, 2013.
U.S. Appl. No. 13/795,556, filed Mar. 12, 2013.
U.S. Appl. No. 13/962,267, filed Aug. 8, 2013.

* cited by examiner

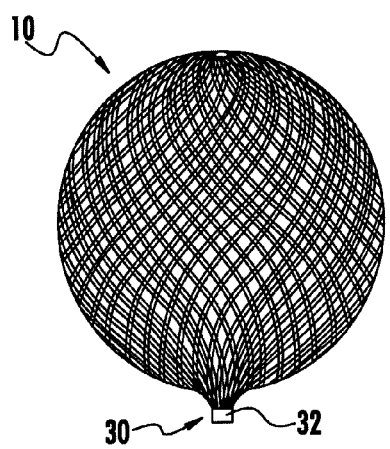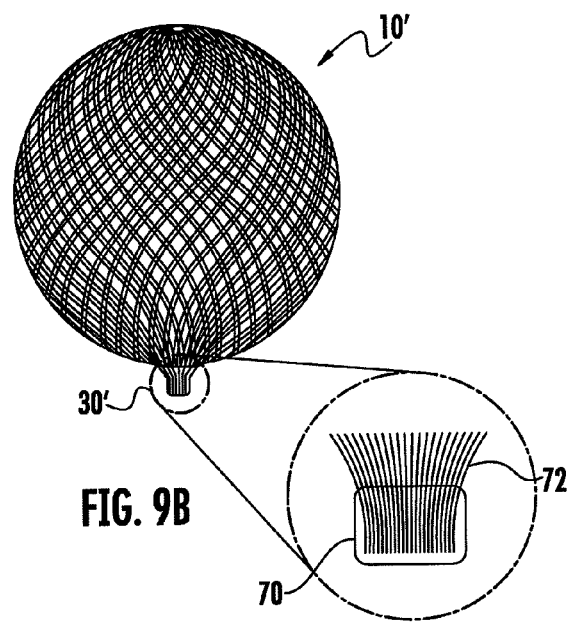
FIG. 9A
FIG. 9B
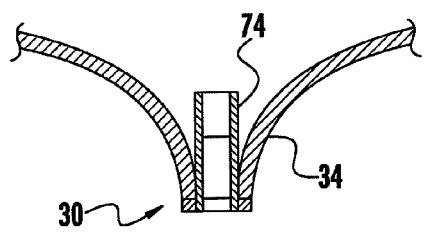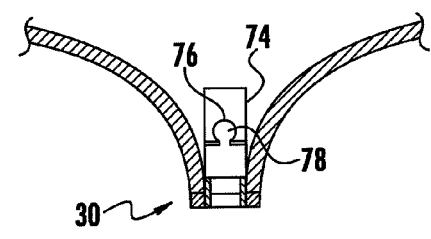
FIG. 10A
FIG. 10B

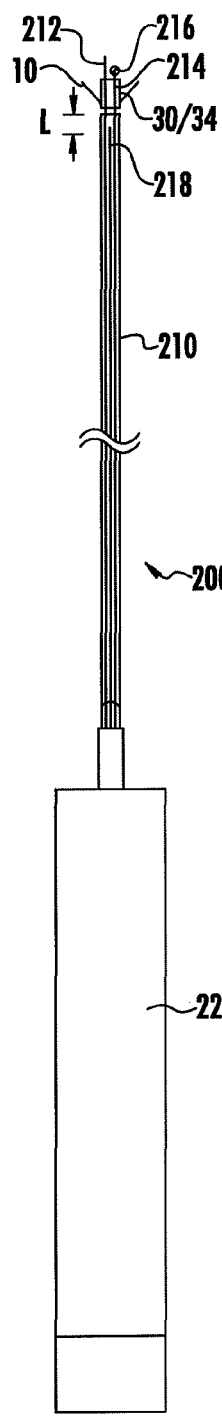
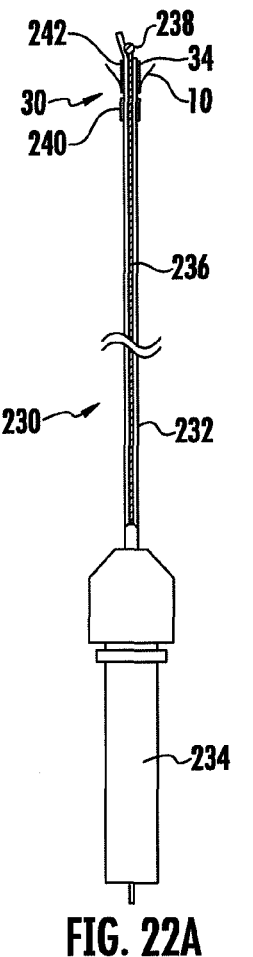
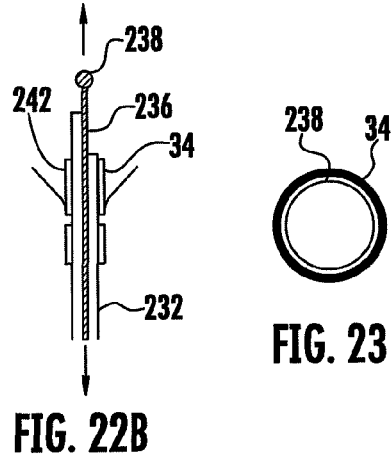
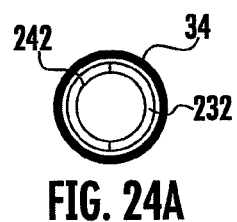
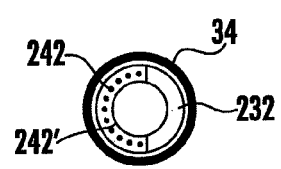
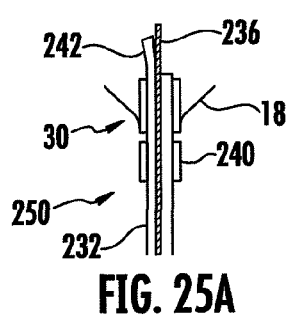
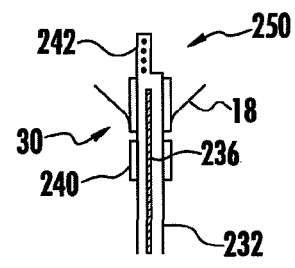
FIG. 21  FIG. 22A  FIG. 22B  FIG. 23  FIG. 24A  FIG. 24B  FIG. 25A  FIG. 25B

BRAID BALL EMBOLIC DEVICE FEATURES

CROSS-RELATED APPLICATION

This application claims priority to U.S. Provisional Application Ser. No. 61/259,585, filed Nov. 9, 2009, which is incorporated herein by reference in its entirety.

BACKGROUND

Commonly-assigned International Application No. PCT/US2009/041313, now published as WO 2009/132045, describes a new class of braid-based embolization devices and delivery system interfaces. The implants may be used for occluding blood flow at endovascular sites. One use is in intracranial aneurysm embolization or occlusion and another in parent vessel occlusion (PVO) or sacrifice. Improvements to those devices are disclosed herein.

SUMMARY

Braid-ball devices formed with folded-over and folded-flat distal end are among the architectures described in WO 2009/132045. These architectures are the ones best suited for treating brain aneurysms. Distal marker approaches are described that are especially suited for such devices. In addition, proximal end finishing approaches are described that are suitable for these and the rest of the devices described in the '045 publication. All of the features and technologies presented in PCT/US2009/041313 (now WO 2009/132045) are incorporated herein by reference.

Regarding the distal marker approaches, one improvement comprises a tether to/for the distal marker included in the implant. Specifically, with the marker affixed adjacent the distal end of the implant (as in the folded-flat embodiments in the incorporated application), the length of the tether/tie extends to the proximal hub of the implant. It has a length set so that when the implant is compressed, the marker is pulled into alignment with the implant and/or catheter.

When a suture is employed for the tether, it can tie around the interior of the distal fold with minimal interference. However, it may be advantageous to use a wire ribbon (e.g., Pt or Nitinol) for other reasons.

Namely, a tether ribbon (especially when pre-formed into a "V" shape) can be threaded through the gap/hole and around as few as one wire from the braid. So-disposed, there is no interference with the compression of the distal end of the implant. What is more, spring action in the ribbon tether (whether comprising two filaments or trimmed to one after crimping, gluing, welding or otherwise affixing at least one marker) can help position the marker against/across the top of the implant when deployed. Such a ribbon can also contribute to marker radiopacity, thereby allowing a smaller marker size.

Another option is to include fibers and/or other thrombus promoting material in connection with the tether. Whatever material option is selected and/or additional features are provided, the proximal end of the tether is advantageously captured between the layers of braid or between the braid and either one of optional inner or outer bands. It may be glued-in, affixed by welding or otherwise.

Yet another set of improvements concerns the manner in which the implant is finished. By "finished", what is meant is the manner in which the proximal side of the implant is managed to define a hub and/or delivery system detachment interface.

In one advantageous approach, in which use of an inner band is desired for interface with detachment system components (such as those described in the referenced application), processing is done with an elongate hypotube set within the braid. The hypotube (e.g., about 2-5 cm long) serves as a means to hold and manipulate an implant preform construct. In addition, when the tube is trimmed off (or when the final or near-final implant is trimmed off relative to the tube being held) the remaining portion of the hypotube within the implant (now the "inner band") defines the detachment interface lumen. Likewise—especially when a more radiopaque material such as Pt/Ir or CoCr is used for the tube, the same structure will improve and/or offer the requisite radiopacity at the proximal end of the implant.

In all, the approach (optionally characterized as a "sacrificial hypotube length" approach) is useful for gluing but may also be applied in a welding technique. In fact, it may be especially useful in the latter context by providing shielding from weld slag and deformation for the proximal aperture/port to be exposed by trimming the tube to define the inner band in the implant. Namely, after welding, a clean cut can be made (e.g., with a diamond saw, laser cutting, EDM, etc.—as above) and then any deburring (by mechanical action, etching, EP or otherwise) can be performed on the newly-exposed face as desired.

In conjunction with a sacrificial hypotube length approach for gluing, or the original gluing approach described in the referenced application, another advantageous option is offered by a different post-processing step. Namely, after an outer band is used at the proximal end of the implant to define an outer casting boundary for adhesive/glue (e.g., Loctite 4014), it then may be removed leaving the underlying glue casting in place. Outer band removal offers potential to reduce all of the height, diameter and appearance of the size of the proximal feature of the implant. Accordingly, it may assist in developing a system with 0.021" catheter crossing profile.

To facilitate removal, the band may advantageously comprise NiTi alloy (that naturally forms a passivation layer) or it may be coated or otherwise plated. A Titanium Nitride coating may be desirable. Spray mold release (e.g., 3M) or dip-coating in mold release may alternatively be employed to assist in slipping-off the band after adhesive application and curing. Otherwise, the band can be cut off the glue casting.

Another approach for achieving minimal implant hub diameter—while maintaining necessary radiopacity—involves affixing a platinum band on top of an inner NiTi band (i.e., in a linear arrangement). The proximal/lower NiTi section can be easily welded to the NiTi braid in the ball (when so-constructed) and the Pt (including Pt/Ir and other alloys) provides an in-line radiopaque marker. The detachment system control and anchor wires are received through both bands. The bands may be attached (e.g., by welding, gluing or soldering) or merely associated with each other until detachment system wire removal. In either case, they may include interference fit, puzzle-piece or other groove or tongue-and-groove features to make or assist in making a connection between the bodies.

Another set of improvements concerns shaping the distal end of a "folded-flat" type implant. It may be provided with a flattened top. The flattened top derives from a flat formed in the round tooling over which the braid is shaped. The flat can be produced by milling about 0.010" off the form. This depth cut allows sufficient "table" for desired shaping and can be consistently applied across a range of implants sized from about 5 mm to 12 mm in diameter with little effect on the perceived shape. The resulting crease in the implant wire shaped by such a form offers an immediate advantage to implant deployment. With the flat placed so close to the distal end of the device, shape recovery of the bend/crease around the flattened top drives early opening of the implant when unsheathed (as compared to a situation where a crease formed around the flat is set further away—or none is provided).

Yet another set of implant improvements described herein augments the density of the ball. Stated otherwise, provision is made for an additional layer of braid material to further decrease the braid matrix porosity, and possibly do so without any increase in device crossing profile/delivery (micro)catheter compatibility.

These improvements involve a third layer of braid that is added to the two layers preferably already present in the folded-flat base implant architecture. In one variation, a third layer of braid is captured between the two layers and captured within the hub region, but trimmed proximal to the distal folded-over/flat section. In another variation, an inner layer is set within the envelope of the aforementioned two layers. It is advantageously attached to a distal end of the inner marker band (above/distal) to any outer marker band provided. As such, the braid's attachment will not increase the hub profile. To avoid any profile increase at the distal end of the implant, the inner layer will typically be trimmed so its compressed length is located proximal to the folded-over braid at the distal end of the implant when compressed. In its unconstrained form, the inner layer may simply define a cup. Alternatively, it may define a secondary ball shape. Such a ball shape may be substantially spherical or ovoid. One advantageous configuration further includes unterminated distal ends to the braid. The ends of the braid defining the inner ball may be secured in a band or welded together. So-configured they can offer another radiopaque marker feature within the ball. However, it may be preferred that the braid ends of the inner layer (in cup, ball form; or otherwise) are unterminated. As such, they may improve thrombus formation within the body of the implant.

Finally, delivery system improvements are described. The features described are "improvements"—as are the features noted above—in a contextual sense. For example, certain of the delivery system architectures may not be as space-efficient as others. Yet, such larger system(s) may be desirable for reason of reduced manufacturing complexity and/or cost.

The subject implant and delivery devices, kits in which they are included, methods of use and manufacture are all included within the scope of the present description. A number of aspects of such manufacture are discussed above. More detailed discussion is presented in connection with the figures below.

BRIEF DESCRIPTION OF THE FIGURES

The figures provided herein are not necessarily drawn to scale, with some components and features exaggerated for clarity. Variations from the embodiments pictured are contemplated. Accordingly, depiction of aspects and elements of embodiments in the figures are not intended to limit the scope of the description.

In the figures,

FIGS. 9A and 9B show implants employing alternative proximal end finishing approaches, with a detail view in FIG. 9B of a low-profile embodiment;

FIGS. 10A and 10B show additional proximal end radiopaque features as may be employed with various end-finishing approaches;

FIG. 21 shows an optional improvement to the architecture of the same system;

FIGS. 22A and 22B show an alternative delivery system interface engaged and disengaged, respectively;

FIG. 23 is an end-on view of the delivery system interface as pictured in FIG. 22B.

FIGS. 24A and 24B illustrate alternative end-on views of the configuration of a pusher shaft in the same system;

FIGS. 25A and 25B show alternative delivery system interface options (engaged and disengaged, respectively) based on the pusher shaft configuration in FIG. 24B;

DETAILED DESCRIPTION

Various exemplary embodiments are described below. Reference is made to these examples in a non-limiting sense, as it should be noted that they are provided to illustrate more broadly applicable aspects of the devices, systems and methods. Various changes may be made to these embodiments and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

To the extent any dimensions are stated in the summary or detailed description, such are intended to be merely examples and are not to limit the inventive subject matter unless explicitly recited in the claims.

Furthermore, the various features of the embodiments described herein are intended to be complement each other and are not intended to be purely alternatives unless stated so.

In other words, features from one embodiment may be freely combined with features of another embodiment, as one of ordinary skill in the art will readily recognize, unless it is stated that those features are only to be used in the alternative. Applicants therefore intend this paragraph to provide written support for any present or future claim that recites features taken from different embodiments, should such not already be clear from the summary, detailed description, and claims.

Figure 1A:
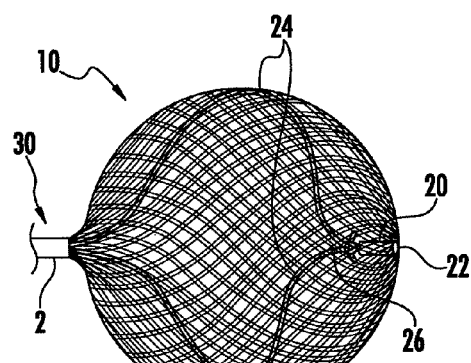
FIGS. 1A and 1B show an implant with a marker tether as expanded and being compressed, respectively.
Figure 1B:
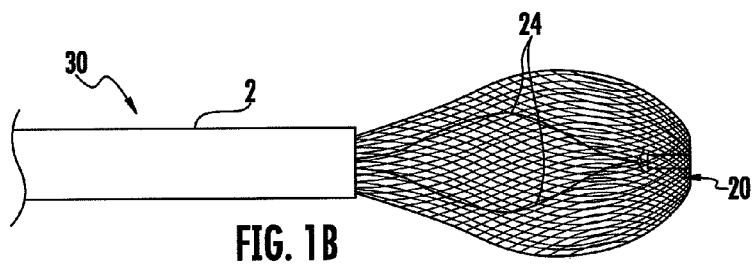

Turning to the figures, FIGS. 1A and 1B show an implant 10. In FIG. 1A, only the hub (not visible) of implant 10 is received within a sheath or catheter 2. Roughly 40% of implant 10 is received within sheath 2 in FIG. 1B. A radiopaque marker 20 (e.g., a Pt band) is visible in both views. As in WO 2009/132045, and with further reference to FIG. 4, implant 10 includes a tie 22 positioned between braid layers 12 and 14 adjacent a distal fold 16 in the braid, which defines aperture 18 (also referred to herein as the hole or gap in the braid). Marker 20 is held by tie 22. Tie 22 may also assist in closing or limiting the size to which aperture 18 may open.

While tie 22 terminates adjacent marker 20 in WO 2009/132045, it extends to proximal hub 30 of implant 10 in the present description. The extension "tether" portions, or members 24 so-provided operate to ensure axial alignment of marker 20 when implant 10 is captured (especially when re-capturing) in a catheter/sheath.

The length of tether member(s) 24 is therefore set such that slack is present when the implant is expanded (as shown in FIG. 1A) and the slack is removed when the implant is fully compressed or tending thereto (as shown in FIG. 1B).

Whereas the tie and/or tether member(s) 24 shown in FIGS. 1A and 1B is typically made of suture material, it may be made of any other biocompatible material including stainless steel, titanium, Nitinol (possibly wire that is martinistic at body temperature-commonly referred to as "muscle wire"), and the like. When suture material is employed it can tie around the interior of distal fold 16 with minimal interference and be knotted at point 26 (see FIG. 1A) to easily secure the position of marker 20. The same approach may be accomplished with fine wire (e.g., 0.001 inch round wire.

It may instead be advantageous to use a wire ribbon (e.g., Pt or Nitinol) for other reasons. A construction as detailed in the next figures was made using a superelastic NiTi ribbon with dimensions set at about 0.001 inches by about 0.003 inches.

Figure 2A:
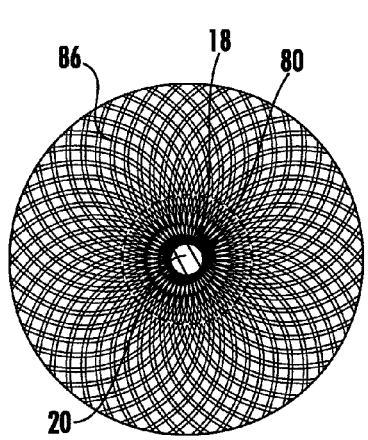
FIGS. 2A and 2B show the distal end and a side view of another tethered-marker embodiment, respectively.
Figure 2B:
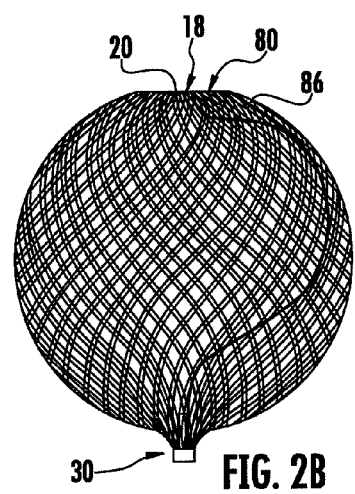
Figure 3:
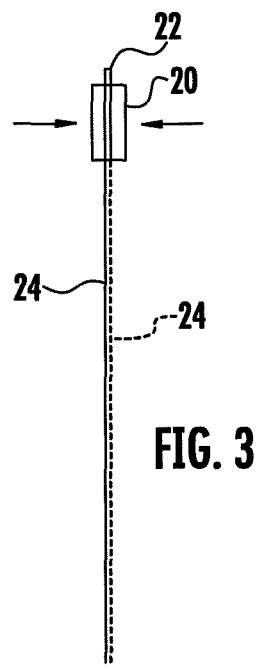
FIG. 3 is a detail view of a marker/tether subassembly.
Figure 4:
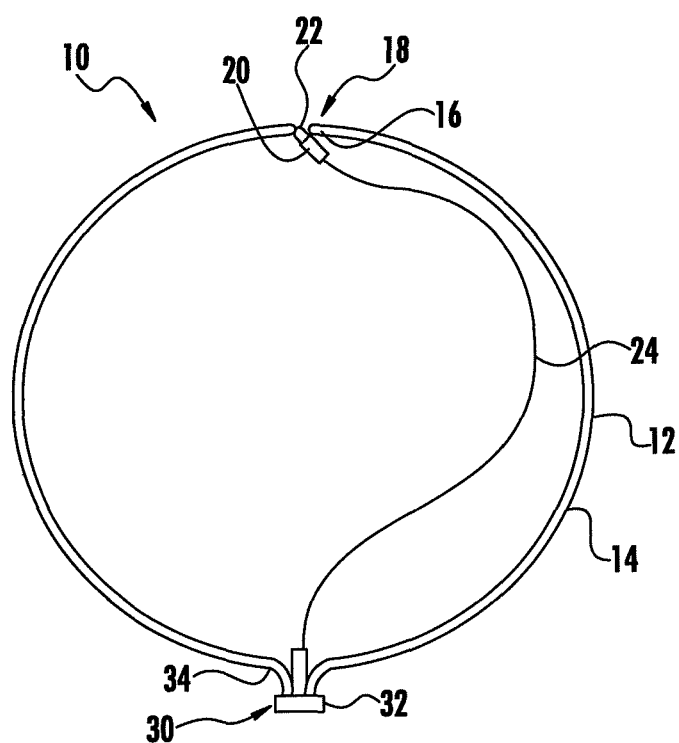
FIG. 4 diagrammatically illustrates the assembly in FIG. 3 set within an implant.

A tether ribbon 22 heatset into a tight loop or "V" shape was threaded through gap 20 and around as few as one wire from the braid at a distal end of implant 10 as shown in FIG. 4. So-disposed, tether ribbon 22 does not substantially interfere with compression of the distal end of the implant. What is more, spring action in the tether ribbon (whether comprising two filaments or trimmed to just one filament (as indicated by the broken line) after crimping, gluing, welding or otherwise affixing marker 20 as shown in FIG. 3) can help position marker 20 against (or across) the top of implant 10 when deployed, as shown in FIGS. 2A and 2B. As for affixing the marker, it is notable that the paired ribbon sections, stacked upon each other, provide a good interface upon which to crimp marker 20 without drastically altering the marker's shape.

Also, the length of the tether may optionally be set in a general "question-mark" shape to match (or more closely match) the curvature of the implant when unconstrained (e.g., as the tether appears in FIG. 4). Pre-shaping the tether to "match" (or approximately match) one or more implant sizes can help ensure predictable and similar performance of implants across a range of different implant sizes and compressions.

Figure 5:
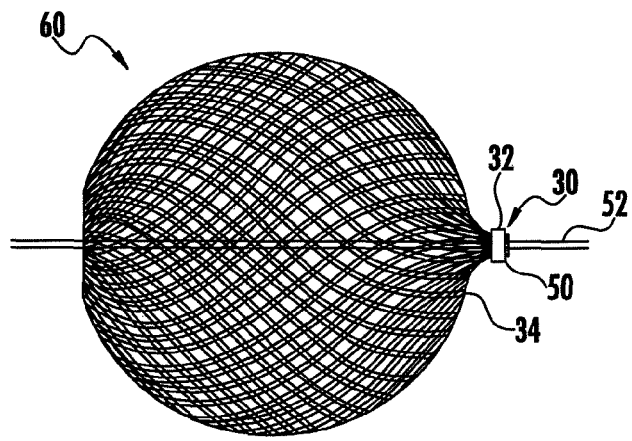
FIG. 5 shows an implant preform prepared for proximal end finishing.

As stated above, another improvement to the subject implants concerns the manner of proximal end finishing. FIG. 5 shows an implant preform 60 prepared for proximal end finishing. Here, implant preform 60 such as prepared in WO 2009/132045 is prepared, leaving an additional overhang section 50 extending past a proximal marker band 32. In many respects, the setup resembles that shown in FIG. 13A of the '045 publication with the implant preform 60 including an inner NiTi tube 34 and the assembly set upon a mandrel 52. To maintain the position of the components as shown, glue (e.g., Loctite 4014) is applied. Even so, and referring also to FIG. 6, the hub region 30 can be welded effectively with a weld bead 54 incorporating the overhanging braid 50, inner tube 34 and at least tack-welding an outer Pt band 32. It is noteworthy that achieving such a near-optimal welding result through (or into) the glue stabilized braid was a surprising result. In other words, it was neither predictable nor expected by those of skill in the art of welding (laser or otherwise). In any case, the length of the braid overhang incorporated into weld 54 may vary depending on a number of factors including implant diameter, wire diameter, braid density, etc. As shown, the overhang is about 0.005 to about 0.010 inches in length.

Figure 7:
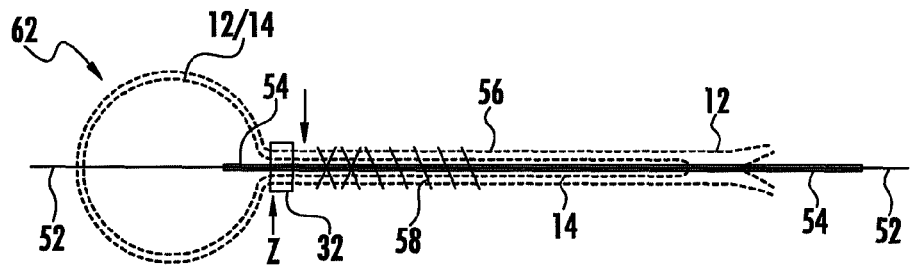
FIG. 7 shows an implant preform prepared for proximal end finishing according to another approach.

Another proximal end finishing approach is described in connection with FIG. 7. Specifically, preform 62 is not trimmed and stabilized for welding as shown in FIG. 5. Rather, preform 62 is prepared upon an elongate hypotube 54. The hypotube body provides a means to hold the construct and stabilize its elongate "tail" section 56 of braid layer 12 and/or layer 14 (e.g., by a wrap 58) thereon.

With a narrow window defined (e.g., with about 0.010 to about 0.025 inches of—preferably—exposed braid) laser energy is applied as indicated by the larger area. The energy is sufficient to weld the braid to the hypotube. The welding process does not, however, weld the hypotube to the optional underlying mandrel 52.

Figure 8:
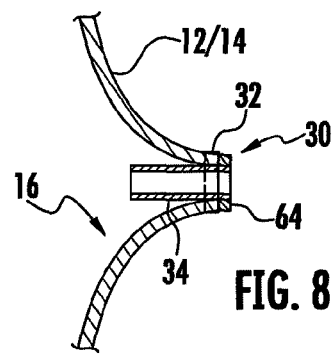
FIG. 8 shows the proximal end cut and welded.

After such welding, the majority of the length of hypotube 54 is "sacrificed". It is trimmed-off to define the inner band 34 of the implant as shown in FIG. 8. This inner band may provide some or all of the radiopacity required in the hub region 30. However an outer band (especially if it comprises Pt) can be tack welded to the braid as indicated by the arrow Z in FIG. 7.

Figure 6:
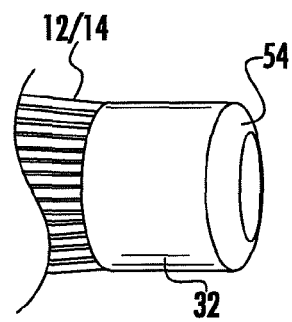
FIG. 6 shows the proximal end welded.

Irrespective of whether an outer marker band is included, FIG. 8 illustrates an advantage of the finishing approach, namely, the avoidance of weld bead flow artifacts associated with surface tension at the end of a body (as seen in FIG. 6). Rather, the weld 64 is neatly faced and the inner lumen of the remaining band 34 de-burred and/or reamed. Both actual and apparent hub size can be minimized accordingly.

FIGS. 9A and 9B illustrate another advantageous proximal end finishing approach for minimizing proximal hub size. FIG. 9A shows an implant with an outer marker band 32 as it will generally appear as affixed by glue or welding. In instances where such a band is affixed by glue, once a glue cast is formed therein the band can be removed. An implant 10' will then include a proximal hub 30' that is reduced in diameter (by as much as about 0.004 inches depending on band thickness) and is also less noticeable by offering less contrast. Outside the body (e.g., in packaging) a physician will see a glaze or sheen of adhesive/glue 70 as a cast 72 in which the braid is embedded instead of a high contrast marker 32.

While seemingly unimportant to function, this visual aspect can indeed be relevant. The impression of physicians regarding the bulk of the proximal feature can affect whether the physician adopts the product. Conventional implants have been designed with the proximal hub completely inset within the inner volume of the implant. This is done to make the implant's appearance more attractive to physicians. However, the implant suffers in performance as a result (e.g., the implant is more difficult to recapture; the requirements on the implant's wire size and strength are heightened to force the implant to recover the inset shape, leading to an undesirable increase in implant dimension; and other performance deficiencies). In the present aspect of the invention, the perceived hub size is reduced, which increases the visual appeal without compromising performance.

Figure 18:
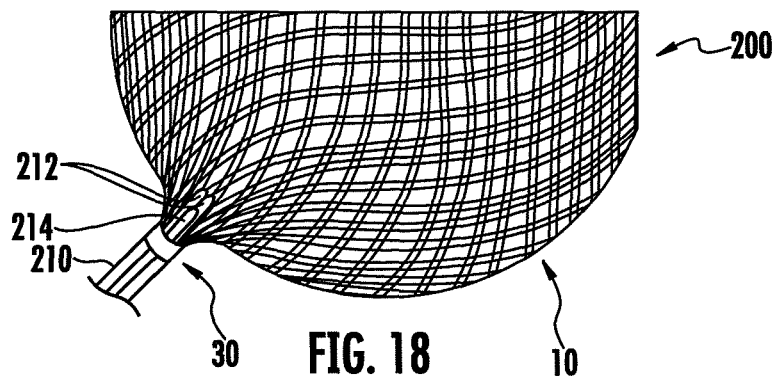
FIG. 18 shows an overview of an implant/detachment system interface as may be employed in connection with the present invention.

FIGS. 10A and 10B illustrate additional embodiments that eliminate the outer band while providing relatively increased radiopacity. Specifically, minimal implant hub size can be achieved by relocating a radiopaque band feature to an in-line arrangement with the inner band 34. A simple Pt band 74 can be set atop the inner band 34 as shown in FIG. 10A. These members may be joined using conventional techniques (i.e., gluing, soldering, welding, etc.) or be held in relation to one another on a temporary basis by utilizing delivery system interface members as shown in FIG. 18, etc. to the embodiment of FIG. 10B interlocks members 34 and 74 through the use of lock 76 and key 78 features.

Figure 11:
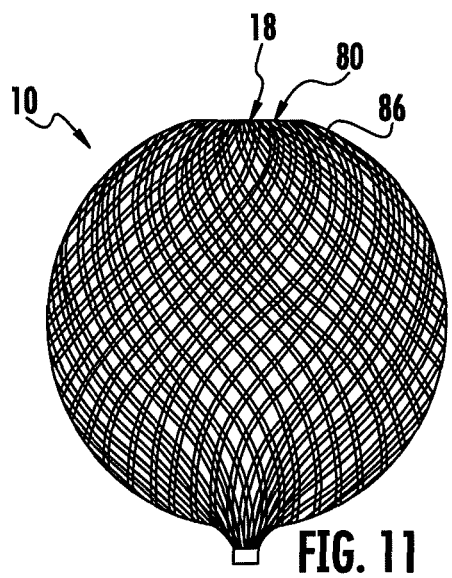
FIG. 11 shows in implant formed with a distal flattened top.
Figure 12:
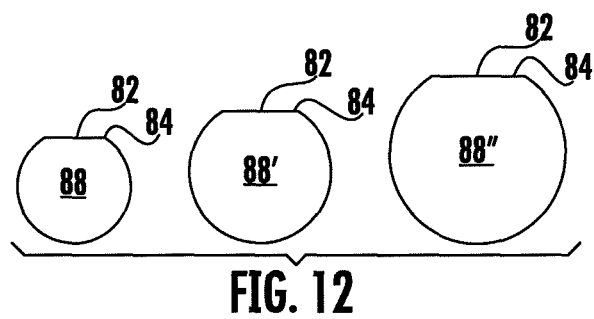
FIG. 12 shows implant forms for imparting an implant shape as shown in FIG. 11 across a number of different implants of a given size range.

Another implant feature is illustrated in connection with FIGS. 11 and 12. The implant optionally includes a flattened top 80 adjacent distal aperture 18. The flattened top is generated by providing a table surface 82 in the molding element 88 used to define the bulk shape of the implant. Molding elements, or "forms," in different sizes 88, 88' and 88" are shown in FIG. 12. They are milled down from a spherical form to define flat 82 surrounded by edge 84. The edge produces a crease 86 in the braid wire. Note that flat 80 and crease 86 are shown in alternate views in FIGS. 2A and 2B.

Figure 13A:
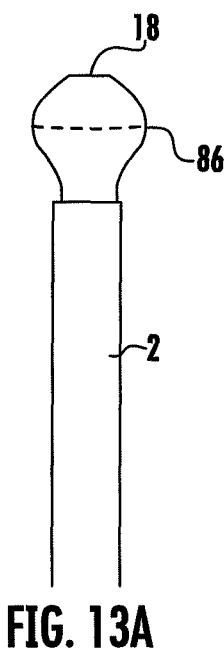
FIGS. 13A and 13B, respectively, illustrate the operation of an implant shaped according to FIG. 11/12 as compared to one that is not.
Figure 13B:
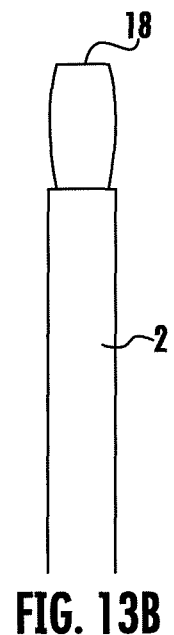

During implant preform heatsetting, it has been found that the flat section improves the quality of the distal fold 16 in the implant, helping to maximize uniformity and minimize the bend radius in the wires. As such, device trackability through tortuous anatomy within a catheter is also improved. The crease at the edge of the flattened area set in the implant also helps with delivery performance upon deployment. Specifically, as illustrated in FIG. 13A, the crease 86 represents multiple bends in the wires forming the implant braid matrix. Upon exit from the microcatheter, the bends recover and cause the implant distal end to open more than an implant without such a crease as shown in FIG. 13B (see also, the implant in FIG. 1B). As a more open body, the implant is softer, with more relaxed braid angle should it contact any fragile tissue—such as the dome of an aneurysm.

Other architectural changes or augmentations that may be applied to implants are shown in FIGS. 14-17. Each approach offers the potential for diagrammatically improved density relative to the parent architecture illustrated in FIG. 4.

Specifically, implant 90 includes an intermediate braid layer 92 set between outer layer 12 and inner layer 14. Layer 92 is captured in hub 30 as are the other layers at a proximal attachment 94. The distal extent 96 can be set at a number of positions. Advantageously, it extends to around the half-way point or equator of the device. This way, the layer will contribute to implant density (or—stated otherwise—reduce porosity) even for wide-neck aneurysms.

Figure 14:
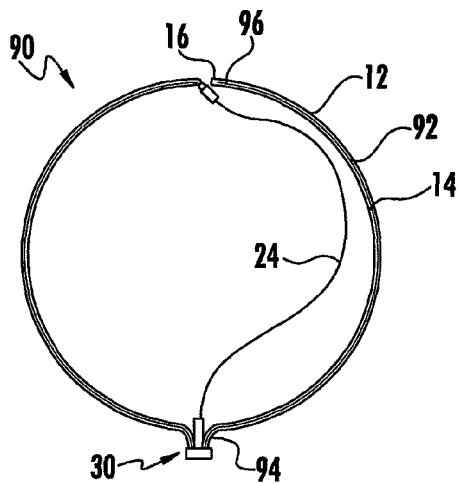
FIGS. 14-17 diagrammatically illustrate improved density implants as compared to the architecture presented in FIG. 4.

As shown in FIG. 14, the distal extent 96 of the braid is adjacent to the folded-over section 16 of the implant. Here, the density is highest so the inner layer wires will tend to stay best trapped between layers 12 and 14. Yet, since the ends 96 do not interfere with the fold 16 (which can be the highest profile aspect of the implant) little or no increase in crossing profile need result.

In production, the inner layer 92 of the implant can be produced simply by cutting a preform (like preform 62) in half at the distal fold. This produces a set of two inner layer sections that can be used in two different devices from a single formation procedure. However produced, because the inner layer may rely on the other layers for structural definition, it may be made of finer wire and/or with lower braid count than the other layers. For instance, the inner layer may comprise 72-end 0.0008 inch wire braid, whereas the outer layers comprise 96-end 0.0008 inch wire braid. However, the reverse may be true, in which the inner layer is more robust. In any case, it may be advantageous to mismatch the number of wire ends included in the braid (such as in the example directly above) to help avoid wire match-up, thereby minimizing porosity.

Figure 15:
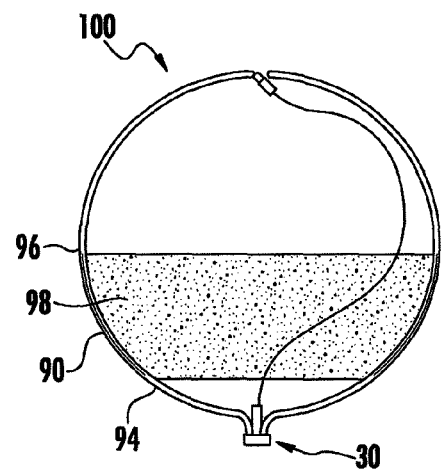

Implant 100 shown in FIG. 15 illustrates another advantageous approach to improving flow disruption effect, without increasing device crossing profile. As in device 90, an intermediate braid layer 90 is employed. However its proximal end is not secured within the hub, thereby easing space constraints in that region.

Instead, braid matrix integrity is maintained by coating the braid layer with a polymer (e.g., TICOPHILIC coating by Lubrizol, Inc.) or other coatings or processing. Hydrogel coating also offers an appealing option, such as a hydrogel-based polymer network capable of entrapping therapeutic agents as described in U.S. Pat. No. 6,905,700 to Won et al. Likewise, while the implant elements advantageously comprise Nitinol braid (typically superelastic NiTi), the braid used for any of the layers may instead comprise polymer—especially high strength biodegradable polymer such as MX-2 (MAX-Prene), synthetic absorbable monofilament (90/10 Glycolide/L-Lactide) and/or G-2 (Glycoprene), synthetic absorbable monofilament (Glycolide (PGA), ε-Caprolactone (PCL), Trimethylene Carbonate (TMC) Copolymer) that is heat set into shape (e.g., at 110 degrees centigrade for an hour) and/or coated with the same to stabilize the braid matrix as described.

Figure 16:
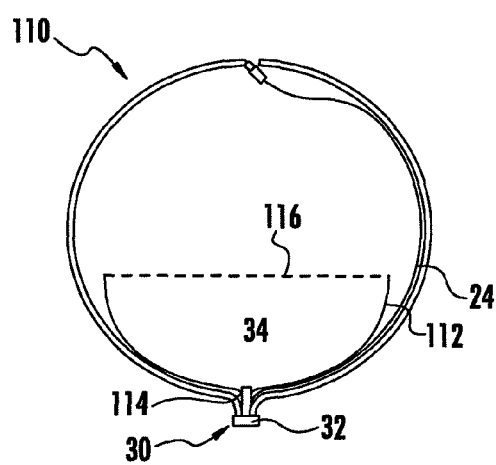

Implant 110 shown in FIG. 16 offers another yet another approach for improved embolizing (or flow disrupting) effect with little or no effect on crossing profile. Such effect is accomplished by affixing an innermost/third braid layer 112 to inner band 34 at its proximal end 114. It may be welded, glued, soldered or otherwise affixed thereto. The distal end of the braid 116 may be trimmed and formed as shown or otherwise. For example, the cup so-formed may closely follow the inner periphery of the device up to or past its equator.

As with variations in the previous figures, the third layer incorporated in the implant simply deploys and recaptures in unison with the rest of the implant. Unique, however, to the architecture of FIG. 16 is that the proximal end 114 of the braid is stably secured, but secured such that it does not require space in the hub (e.g., within the outer marker band 32) without dimensional stackup.

Figure 17:
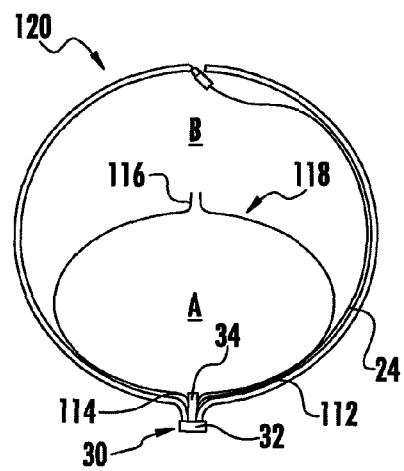

A related implant configuration is shown in FIG. 17. Here, in implant 120, the same proximal end 114 attachment approach is employed. Yet, instead of forming (e.g., by heatsetting) the inner layer of braid into a cup shape, an inner ball 118 is formed. The proximal side of the ball improves overall proximal-side implant density, and also defines separated flow stagnation zones A and B within the implant to further assist in thrombus formation within the implant.

Inner ball body 118 may be shape set over a form. Alternatively, and more advantageously, the shape can be formed without either an external or internal form by bunching the braid up and tying it onto a mandrel for heatsetting. Such a "free-forming" approach is functionally advantageous because it maximizes braid angle (hence, density) in the final body. Yet, any resulting inconsistency in shape is manageable given that the only outer body of the implant defined by braid layers 12 and 14 is in contact with an aneurysm.

Irrespective of how it is formed (and the particular braid configuration selection) the inner ball 118 within the architecture will be configured so that it will not interfere with the distal end of the implant body/shell and/or marker and tether when the device is compressed for delivery or recapture.

Figure 19A:
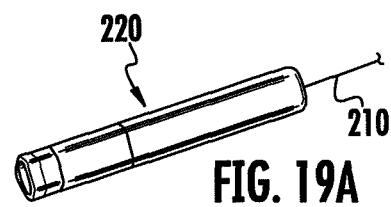
FIGS. 19A-19E and 20A-20E illustrate the stages of operation (handle-side and implant-side, respectively) of the system shown in FIG. 18.

More generally, FIG. 18 provides an overview of implant-side of a treatment system 200. The system includes an implant 10 (90, 100, 110, 120) and a pusher/catheter shaft 210 ultimately attached to a handle 220 (e.g., as shown in FIGS. 19A-19-E). Any of these may be constructed according to the teachings herein and/or incorporated by reference.

Figure 19B:
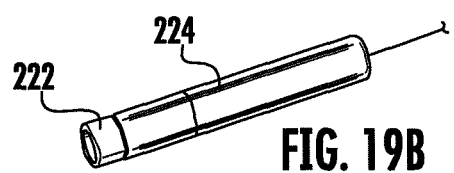
Figure 19C:
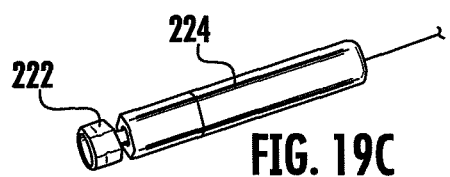
Figure 19D:
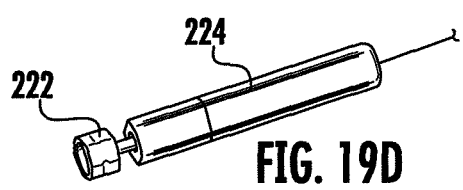
Figure 19E:
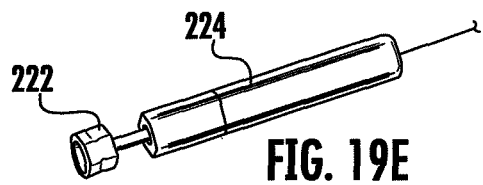
Figure 20A:
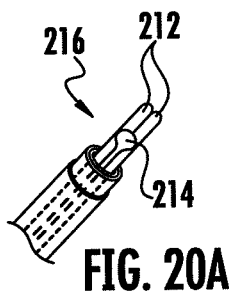
Figure 20B:
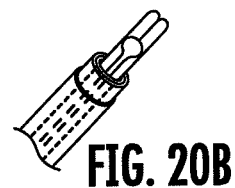
Figure 20C:
Figure 20D:
Figure 20E:
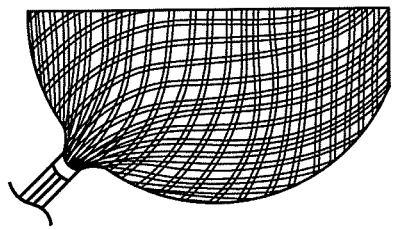

One handle construction includes a single plunger. The plunger pulls a collar that progressively engages and pulls sockets connected to the wires; first each control wire 212 is pulled (one at a time), then the anchor wire 214. Such action is illustrated in FIGS. 19A-19E and 20A-20E. FIGS. 19A and 20A show the device components as removed from packaging. FIG. 19B illustrates unlocking the handle plunger 222 with a 120 degree rotation relative to handle body 224. Such action has no effect on the detachment interface 216 shown in FIG. 20B. However, progressive pull of the plunger in FIGS. 19C-19E effect the release of the system as shown in FIGS. 20C-20E.

FIG. 21 shows an optional improvement to the architecture of system 200. Here, system 200' has only one "true" control wire 212 is received within the hub or inner band 30/34 of the implant 10. Even so, the implant remains securely/stably attached to the catheter shaft by virtue of the control wire interaction with anchor ball 216 (e.g., as formed by laser or as otherwise configured).

Release of the implant is effected as if progressing from the steps in FIGS. 19C and 20C to 19E and 20E. However, a third (floating or actuated) "dummy" wire 218 is still loaded within the lumen of pusher shaft 210. Use of this wire maintains a close-packed arrangement of the wires inside shaft 210, which can be important in determining wire position within a tortuous setting. Yet, release angle may be increased and plunger pull force reduced because the wires within the implant have more space between them allowing for spatial accommodation.

Note that the length "L" by which wire 218 is inset within the pusher shaft may vary depending on purpose. It may have no inset (i.e., essentially abut the implant proximal end). It may be inset by about 1 mm so that any forward motion in a tortuous setting does not result in contact with the implant. Or it may be inset to a greater degree (e.g., between about 1 cm and 5 cm) to improve distal tip flexibility of delivery pusher shaft 210.

FIGS. 22A and 22B show an alternative delivery system interface in engaged and disengaged states, respectively. Here, system 230 comprises a catheter/pusher shaft 232 actuated with the assistance of a typical torque 234. Torquer 234 locks a position of a central wire 236 including an anchor ball for implant 10 delivery. A bumper or shoulder 240 may be affixed to the catheter (optionally a Pt band also serving as a marker) to abut a hub 30 of the implant for pushing.

Engagement is achieved between the implant and pusher shaft by virtue of extension 242 that is offset into an interfering relationship with an inner band 34 of the implant when the anchor ball 238 is in a retracted position as shown in FIG. 22A. When wire 236 (and its terminal ball feature 238) is advanced as shown in FIG. 22B, extension section 242 is free to move (e.g., to return to its original position by elastic action or upon catheter shaft withdrawal) and slide out of the implant.

FIG. 23 is an end-on view of the delivery system interface as pictured in FIG. 22B. As shown, no interference between the ball 238 and/or extension persists once wire 236 is advanced. FIG. 24A portrays a similar view without the wire in place. It shows extension 242 and catheter body 232. And while they are illustrated as formed in one manner (i.e., with a 90 degree cut-down), it is to be appreciated that the extension may instead be formed by an angular cut or otherwise. Indeed, FIG. 24B shows an approach in which the extension section is formed by pushing over the catheter wall on one side to meet the other and optionally heat setting, fusing or gluing the component parts 242 and 242' together.

FIGS. 25A and 25B show an alternative delivery system interface 250 option (engaged and disengaged, respectively) based on the pusher shaft extension configuration in FIG. 24B. Due to the increased wall thickness offered by the double wall layer, the system can work much as that shown in FIGS. 22A and 22B, except without need for a distal interference feature (i.e., anchor ball/band). As such, withdrawal of wire 236 will relieve the interference and unlock the pusher shaft 232 (specifically, the associated extension) for withdrawal from the implant 10.

Figure 26:
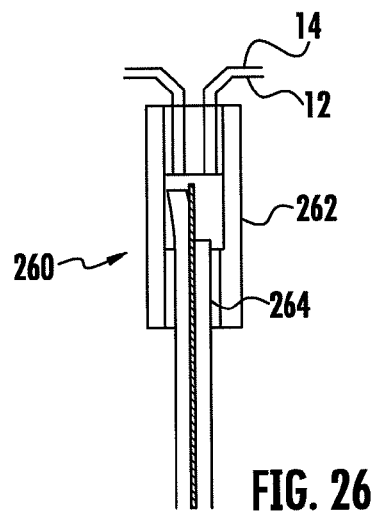
FIG. 26 shows an alternative implant-side interface with a delivery system as presented in FIGS. 25A and 25B.

FIG. 26 shows an alternative implant-side interface with a delivery system as presented in FIGS. 25A and 25B. Here an implant socket 260 is provided. Socket 260 may be defined by a cup 262 attached to one or more implant braid layers (12/14), by welding or otherwise, and a reducer tube 264 threaded, pressed or otherwise affixed in the proximal end of the cup. Note that with such an arrangement that implant pushing can be accomplished without a shoulder or other proximal interface. Instead, both push and pull (for withdrawal) force application can occur within the socket chamber. While such a socket will typically be larger than the previous interfaces shown, it is easily retrofit or used as and alternative to the screw-type release approaches employed in many vessel sacrifice and closure devices as sold by AGA Medical, Inc. and others.

Figure 27:
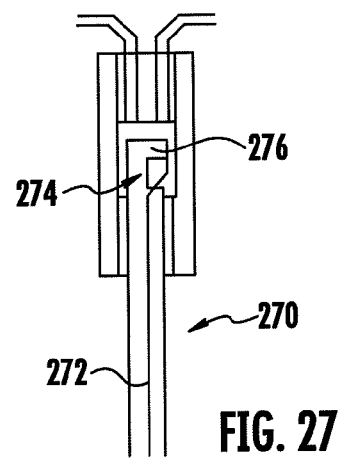
FIG. 27 shows an implant-side interface like that presented in FIG. 26 with an alternative pusher-side architecture.

The delivery system configuration in FIG. 27 shows the same implant-side interface 260, with an alternative pusher-side engagement/disengagement (or latch) architecture 270. This architecture is a simplified version of that shown in FIG. 18 of WO 2009/132045. Specifically, a pusher shaft 272 (e.g., metal hypotube) is provided with a single window cutout 274. The window (configured as a square cutout, rounded, or a simple kerf) allowing a core member 276 (e.g., NiTi ribbon) to pass therethrough and provide interference against pusher shaft distal face 276 to prevent delivery system detachment until core member withdrawal.

Figure 28A:
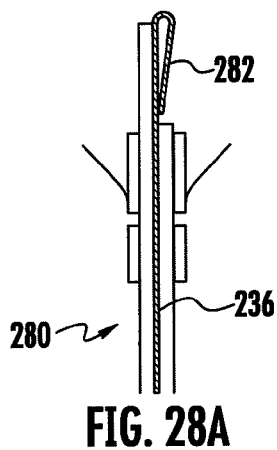
FIGS. 28A and 28B show an alternative engagement/disengagement interface for a system like that shown in FIGS. 22A and 22B.
Figure 28B:
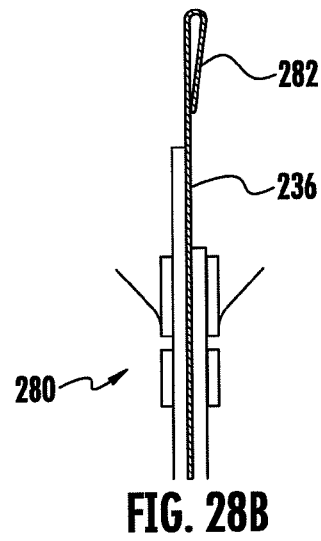
Figure 29:
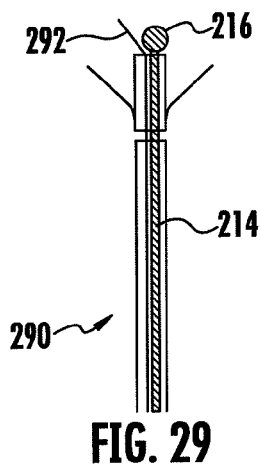
FIGS. 29 and 30 show yet another engagement/disengagement architecture for each of a braid-type implant and embolic coil, respectively.

FIGS. 28A and 28B show an alternative latch interface 280 for a system like that shown in FIGS. 22A and 22B. In this system, a bent back wire hook 282 serves the function of the ball in the former system. Such a system offers the advantage of very low cost production, as well as a secure anchoring feature. FIG. 29 shows a system 290 most closely related to that in FIG. 21, except that multiple control and/or dummy wires are replaced with a single ribbon 292.

Figure 30:
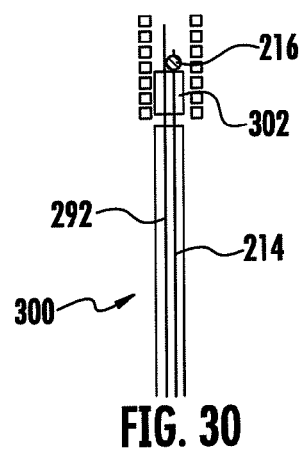

Finally, FIG. 30 shows a detachment system 300. As in system 290 a ribbon 292 may be used in conjunction with a round anchor wire 214 with a ball-shaped anchor 216. An alternative approach that may be used in either system is to employ a ribbon as the "anchor wire" and form the interference feature at its end by tying a knot therein (as a substitute for a laser-formed ball). Such a knot can be shape set, glued or welded to stabilize its shape. It can be reliably be produced at low cost at a very small size, on a ribbon. A socket-type interface can be formed within the coil by fitting a collar feature 302 within its proximal end. The collar may be threaded-in (i.e., into the coils like a thread pitch). An alternative approach involves flowing solder between the coils and defining a lumen therein using a removable mandrel. The mandrel may be prepared in any manner to facilitate its removal, including those described for the removable hub in connection with the improvement described in connection with FIG. 9B.

In the various delivery system architectures, the catheter/pusher shaft comprise a simple extrusion (e.g., PTFE, FEP, PEEK, etc.) or may be constructed using conventional catheter construction techniques and include a liner, braid support and outer jacket (not shown). An exemplary construction is available through MicroLumen, Inc. as Braid Reinforced Polyimide. A distal section of the Polyimide may be ablated and replaced with fused Pebax to provide a softer or progressively-flexible end to the catheter. A loading sheath is typically provided over the pusher shaft. Advantageously, the loading sheath is splittable.

If not preloaded, after removal from sterile packaging (not shown), the implant is pulled into the loading sheath. The loading sheath is received within the hub of the catheter to be used for implant delivery and the implant is advanced into the catheter. Then, the implant may be advanced to and deployed at a treatment site. Or it may be retrieved in exchange for another size implant—else repositioned, if desired, prior to ultimate detachment as illustrated in the incorporated patent application subject matter.

In the present invention, the subject methods may include each of the physician activities associated with implant positioning and release. As such, methodology implicit to the positioning and deployment of an implant device forms part of the invention. Such methodology may include placing an implant within a brain aneurysm, or at parent vessel targeted for occlusion, or other applications. In some methods, the various acts of implant introduction to an aneurysm or parent vessel are considered.

More particularly, a number of methods according to the present invention involve the manner in which the delivery system operates in reaching a treatment site, for example. Other methods concern the manner in which the system is prepared for delivering an implant, for example attaching the braid ball to the delivery system. Any method herein may be carried out in any order of the recited events which is logically possible, as well as in the recited order of events, or slight modifications of those events or the event order.

It is contemplated that any optional feature of the inventive variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language. Use of the term "invention" herein is not intended to limit the scope of the claims in any manner. Rather it should be recognized that the "invention" includes the many variations explicitly or implicitly described herein, including those variations that would be obvious to one of ordinary skill in the art upon reading the present specification. Further, it is not intended that any section of this specification (e.g., the Summary, Detailed Description, Abstract, Field of the Invention, etc.) be accorded special significance in describing the invention relative to another or the claims. All references cited are incorporated by reference in their entirety. Although the foregoing invention has been described in detail for purposes of clarity of understanding, it is contemplated that certain modifications may be practiced within the scope of the appended claims.

What is claimed is:

1. An implant comprising:
   a self-expandable body having proximal and distal ends and expanded and compressed configurations,
   a radiopaque marker positioned within an interior volume of the body and held adjacent the distal end by at least one filament coupled to the proximal and distal ends,
   wherein the at least one filament crosses the interior volume of the body extending from the marker and terminating at the proximal end, and
   wherein the at least one filament has a length about equal to a length of the body in the compressed configuration such that (i) the marker is misaligned with respect to a longitudinal axis of the body when the implant is unconstrained in the expanded configuration and (ii) the marker is aligned with the longitudinal axis of the body when the body is in the compressed configuration.

2. The implant of claim 1, wherein the at least one filament comprises suture material, and a first end of the suture material is coupled to a proximal end of the marker and a second end of the suture material is coupled to the body proximal end.

3. The implant of claim 1, wherein the at least one filament comprises metal weldable to the body for securement at the proximal end of the body.

4. The implant of claim 3, wherein the filament is in the form of round wire.

5. The implant of claim 3, wherein the filament is in the form of ribbon.

6. The implant of claim 1, wherein the body comprises a braided layer.

7. The implant of claim 1, wherein the radiopaque marker is coupled to the body.

8. An implant comprising:
   a self-expandable body having longitudinal axis, proximal and distal ends, and expanded and compressed configurations;
   at least one filament, having a length about equal to a length of the body in the compressed configuration, extending within the body and coupled to the proximal and distal ends; and
   a radiopaque marker attached to the at least one filament such that the marker is (i) misaligned with respect to the longitudinal axis in the expanded configuration and (ii) aligned with the longitudinal axis in the compressed configuration.

9. The implant of claim 8, wherein the body comprises a braided layer.

10. The implant of claim 8, wherein the radiopaque marker is coupled to the body.

11. The implant of claim 8, wherein the at least one filament is in the form of round wire.

12. The implant of claim 8, wherein the at least one filament is in the form of ribbon.

13. The implant of claim 8, wherein the at least one filament comprises suture material, and a first end of the suture material is coupled to a proximal end of the marker and a second end of the suture material is coupled to the body proximal end.

14. The implant of claim 8, wherein the at least one filament comprises metal weldable to the body for securement at the proximal end of the body.

15. The implant of claim 8, wherein in the expanded configuration, the at least one filament is slack such that the marker is misaligned with respect to a longitudinal axis of the body, and in the compressed configuration, the at least one filament is aligned with the longitudinal axis.

16. The implant of claim 8, wherein in the collapsed configuration, the body comprises a collapsed axial length that is substantially equal to a length of the at least one filament such that the at least one filament is aligned with the longitudinal axis in the collapsed configuration.

17. The implant of claim 8, wherein a first end of the at least one filament is attached to the proximal end and a second end of the at least one filament is attached to the distal end.

18. The implant of claim 1, wherein the at least one filament is fixedly attached to the distal end of the implant in the compressed configuration.

19. The implant of claim 1, wherein the at least one filament is coupled to at least one of the distal or proximal ends of the body.

20. An implant comprising:
a self-expanding body having a longitudinal axis, proximal and distal ends, and expanded and compressed configurations; and
a radiopaque marker component, having a length about equal to a length of the body in the compressed configuration, extending within the body and having first and second ends being coupled to the respective proximal and distal ends, the marker component being (i) misaligned with respect to the longitudinal axis, and slack under the action of gravity, in the expanded configuration and (ii) aligned with the longitudinal axis in the compressed configuration.

21. The implant of claim 20, wherein the marker component comprises at least one filament.

22. The implant of claim 20, wherein an end of the marker component is fixedly attached to an end of the body.

* * * * *